United States Patent
Nishio et al.

(10) Patent No.: US 10,456,566 B2
(45) Date of Patent: Oct. 29, 2019

(54) BALLOON AND INTRALUMINAL TREATMENT METHOD

(71) Applicant: TERUMO KABUSHIKI KAISHA, Shibuya-ku, Tokyo (JP)

(72) Inventors: Kosuke Nishio, Tokyo (JP); Riyaheh S. Hazama, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 706 days.

(21) Appl. No.: 15/003,387

(22) Filed: Jan. 21, 2016

(65) Prior Publication Data

US 2016/0213900 A1 Jul. 28, 2016

(30) Foreign Application Priority Data

Jan. 22, 2015 (JP) ................................. 2015-010663

(51) Int. Cl.
*A61M 29/00* (2006.01)
*A61M 29/02* (2006.01)
*A61M 25/10* (2013.01)
*A61M 25/00* (2006.01)

(52) U.S. Cl.
CPC ......... *A61M 29/02* (2013.01); *A61M 25/0017* (2013.01); *A61M 25/10184* (2013.11); *A61M 2025/0057* (2013.01); *A61M 2025/1084* (2013.01); *A61M 2025/1093* (2013.01); *A61M 2210/1096* (2013.01)

(58) Field of Classification Search
CPC .... A61M 25/10; A61M 25/104; A61M 29/00; A61M 29/02; A61M 2025/1013; A61M 2025/1043; A61M 2025/1052; A61M 2025/1075; A61M 2025/1084; A61M 2025/109; A61B 17/12109; A61B 17/12113; A61B 17/12136; A61B 2017/22001
USPC .................................................. 606/192–196
See application file for complete search history.

(56) References Cited

U.S. PATENT DOCUMENTS 5,308,325 A * 5/1994 Quinn ................. A61J 15/0015
604/174
6,132,397 A * 10/2000 Davis ............... A61B 17/12109
604/101.02

FOREIGN PATENT DOCUMENTS

JP 2001-198222 A 7/2001

OTHER PUBLICATIONS

Translation of Notification of Reasons for Refusal in corresponding Japanese Application No. 2015-010663 dated Nov. 28, 2018 (3 pages).

(Continued)

*Primary Examiner* — Melanie R Tyson
(74) *Attorney, Agent, or Firm* — Buchanan Ingersoll & Rooney PC

(57) ABSTRACT

A balloon can be rather easily pressed against an inner wall inside a lumen using a proper pressing force. A balloon has a dilating/deflating section that forms a hollow internal space, and that deflates by the internal space being decompressed, and a support section that is arranged in the internal space so as to deflate in response to the deflation of the dilating/deflating section, and that supports the dilating/deflating section so as to dilate outward in a state where the internal space is under atmospheric pressure.

16 Claims, 12 Drawing Sheets

(56) References Cited

OTHER PUBLICATIONS

Translation of Notification of Reasons for Refusal in corresponding Japanese Application No. 2015-010663 dated Aug. 28, 2018 (3 pages).

* cited by examiner

BALLOON AND INTRALUMINAL TREATMENT METHOD

CROSS-REFERENCES TO RELATED APPLICATIONS

This application claims priority to Japanese Application No. 2015-010663 filed on Jan. 22, 2015, the entire content of which is incorporated herein by reference.

TECHNICAL FIELD

The present invention generally relates to a balloon and an intraluminal treatment method.

BACKGROUND DISCUSSION

As treatments for a stenosed site or an occluded site appearing inside a lumen such as blood vessels, urethras, and the like, a treatment is known in which a balloon is pressed against an inner wall inside the lumen such as urethras and the like. Japanese Application Publication No. 2001-198222 discloses a balloon which is used for pressure hemostasis performed on bleeding from a prostatic urethra after transurethral prostatectomy is performed in order to treat benign prostatic hyperplasia.

SUMMARY

When a balloon is dilated for the above-described treatment, it is important to control a pressing force of the balloon pressed against an inner wall inside a lumen such as urethras and the like so as to reach a proper value. Accordingly, for example, the balloon is connected to a pressure sensor so as to monitor pressure. Consequently, a device configuration becomes complicated, and manual skills become cumbersome.

The balloon disclosed here can be rather easily pressed against an inner wall inside a lumen by using a proper pressing force, and the disclosed intraluminal treatment method can apply the proper pressing force.

A balloon disclosed here includes a dilating/deflating section that forms a hollow internal space, and that deflates by the internal space being decompressed, and a support section that is arranged in the internal space so as to deflate in response to the deflation of the dilating/deflating section, and that supports the dilating/deflating section so as to dilate outward in a state where the internal space is under atmospheric pressure.

According to another aspect, an intraluminal treatment method involves creating a negative pressure in a hollow internal space surrounded by a dilating/deflating section of a balloon, with a support section positioned in the internal space; inserting the balloon into a lumen in a living body while the hollow internal space is under the negative pressure; and releasing the negative pressure in the hollow internal space to cause the support section to dilate outwardly in a radial direction and press against the dilating/deflating section so that the dilating/deflating section is expanded outwardly into contact with an inner surface of the lumen in the living body.

According to another aspect, an intraluminal treatment method comprises: inserting a balloon into a lumen in a living body while a hollow internal space surrounded by a dilating/deflating section of the balloon is under the negative pressure; and increasing the pressure in the internal space to a pressure greater than the negative pressure in the internal space during insertion of the balloon into the lumen in the living body. The increase of the pressure in the internal space causes a support section located in the internal space to press outwardly against the dilating/deflating section so that the outer surface of the dilating/deflating section contacts an inner surface of the lumen in the living body According to the balloon and the intraluminal treatment method which are configured as described above, the support section causes the dilating/deflating section to dilate outward in a state under atmospheric pressure. Therefore, a dilated state can be maintained without pressurizing the balloon. Accordingly, the balloon can be easily pressed against the inner wall inside the lumen. In addition, the support section is disposed in order to dilate the dilating/deflating section so as to have a desired outer diameter. In this manner, while wrinkles on an outer surface of the dilating/deflating section are reduced, the balloon can be pressed against the inner wall inside the lumen by using proper pressing force. Therefore, it is possible to provide the balloon which can be easily pressed against the inner wall inside the lumen by using proper pressing force, and the intraluminal treatment method.

DETAILED DESCRIPTION

Figure 1:
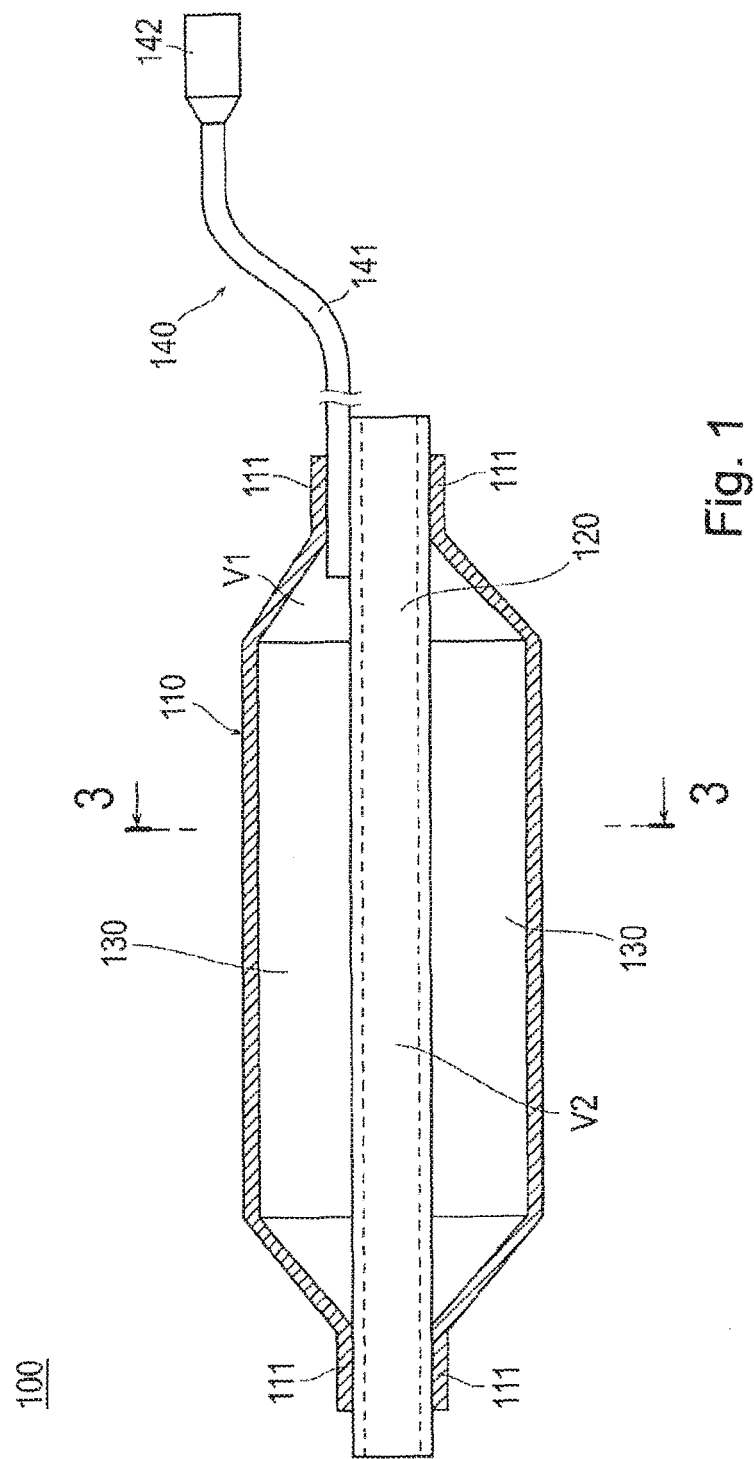
FIG. 1 is a schematic configuration diagram of a balloon according to one embodiment representing an example of the disclosed balloon.

Set forth below, with reference to the accompanying drawing figures, is a detailed description of embodiments of a balloon and an intraluminal treatment method representing examples of the inventive balloon and an intraluminal treatment disclosed here. Dimensional proportions in the drawings may be exaggerated and different from actual proportions for convenience of description. In addition, in the following description, a hand operation side or end of a balloon 100 is referred to as a "proximal side" or "proximal end", and a side or end inserted into a biological lumen is referred to as a "distal side" or "distal end".

Figure 2A:
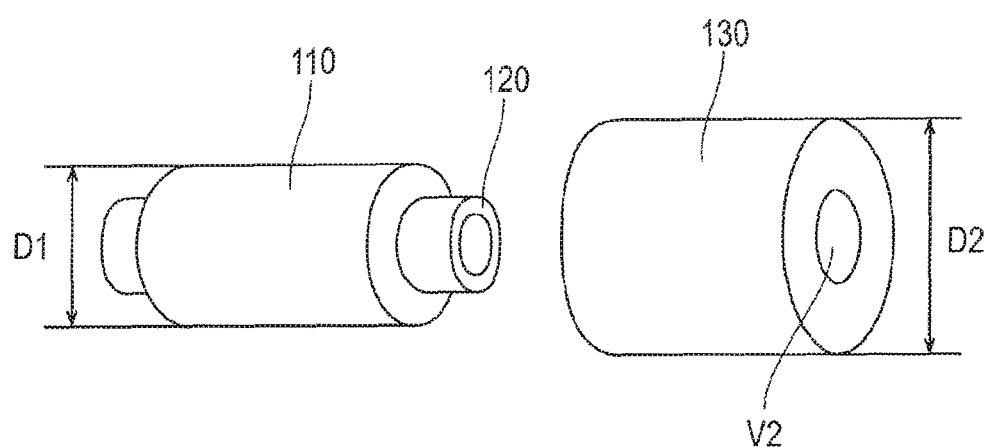
FIG. 2(A) is a perspective view illustrating a dilating/deflating section, an inner peripheral section, and a support section in a separated state under atmospheric pressure.
Figure 2B:
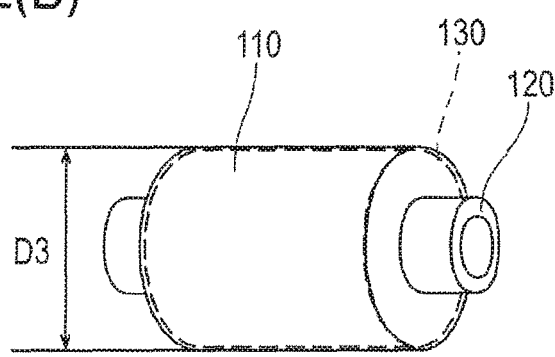
FIG. 2(B) is a perspective view illustrating a state where the support section is arranged inside the dilating/deflating section.
Figure 3:
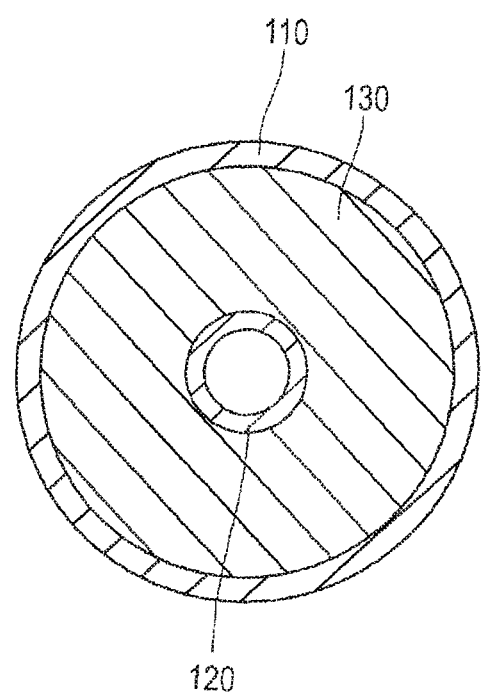
FIG. 3 is a cross-sectional view taken along the section line 3-3 in FIG. 1.

FIG. 1 is a schematic configuration diagram of the balloon 100 according to the embodiment of the present invention. FIG. 2(A) is a perspective view illustrating a dilating/deflating section 110, an inner peripheral section 120, and a support section 130 in a separated state under atmospheric pressure, and FIG. 2(B) is a perspective view illustrating a state where the support section 130 is arranged inside the dilating/deflating section 110. FIG. 3 is a sectional view taken along line 3-3 in FIG. 1.

In brief, the balloon 100 according to this embodiment has the dilating/deflating section 110 that forms or surrounds a hollow internal space V1, and that deflates by the internal space V1 being decompressed or being reduced in volume/size, and the support section 130 that is arranged in the internal space V1 so as to deflate in response to the deflation of the dilating/deflating section 110, and that supports the dilating/deflating section 110 by dilating outward in a state where the internal space V1 is under atmospheric pressure. Hereinafter, a configuration of the balloon 100 according to the present embodiment will be described.

As illustrated in FIG. 1, the balloon 100 includes the dilating/deflating section 110, an inner peripheral section 120, the support section 130, and a fluid supply/discharge section 140.

The dilating/deflating section 110 dilates or expands outwardly so that the outer surface of the dilating/deflating section 110 is pressed against an inner wall inside a lumen. As illustrated in FIGS. 2 and 3, the dilating/deflating section 110 forms or surrounds the hollow internal space V1. Both end portions 111 of the dilating/deflating section 110 are integrally formed with the remainder of the dilating/deflating section 110 and are bonded to an outer periphery of the inner peripheral section 120. A portion between both end portions 111 and the inner peripheral section 120 is sealed.

The dilating/deflating section 110 is flexible, and is formed of an elastic material. Examples of materials for forming the dilating/deflating section 110 include a polymer material such as silicone rubber, latex rubber, polyolefin, cross-linked polyolefin, polyvinyl chloride, polyamide, polyamide elastomer, polyester, polyester elastomer, polystyrene elastomer, polyurethane, polyurethane elastomer, fluororesin, polyimide, and the like, or a mixture of these materials. For example, polyolefin is polyethylene, polypropylene, polybutene, ethylene-propylene copolymer, ethylene-vinyl acetate copolymer, ionomer, or a mixture of two or more of these materials.

As illustrated in FIGS. 2 and 3, the inner peripheral section 120 possesses a hollow cylindrical shape. The inner peripheral section 120 is arranged inside the dilating/deflating section 110. The inner peripheral section 120 dilates (outwardly expands) or deflates (inwardly contracts) in a radial direction in response to an increase or a decrease in pressure in the internal space V1 between the dilating/deflating section 110 and the inner peripheral section 120. Specifically, the inner peripheral section 120 deflates inward in the radial direction by pressurizing the internal space V1 of the dilating/deflating section 110. In addition, the inner peripheral section 120 dilates outward in the radial direction by decompressing the internal space V1 of the dilating/deflating section 110.

The inner peripheral section 120 is flexible, and is formed of an elastic material. The inner peripheral section 120 is formed of the same material as that of the dilating/deflating section 110.

The support section 130 supports the dilating/deflating section 110 so as to dilate (expand) outward in a state where the internal space V1 of the dilating/deflating section 110 is under atmospheric pressure. The support section 130 is arranged in the internal space V1 of the dilating/deflating section 110, and deflates (contracts) in response to the deflation of the dilating/deflating section 110. The support section 130 has an outer diameter having a columnar shape which forms a circular cross section. The support section 130 comes into contact with an inner peripheral surface of the dilating/deflating section 110 and an outer peripheral surface of the inner peripheral section 120. The support section 130 presses the inner peripheral section 120 inward in the radial direction, and supports the inner peripheral section 120 substantially at the center of the circular cross section of the dilating/deflating section 110. The support section 130 is arranged along the inner peripheral section 120. The support section 130 may be bonded to at least any one of the dilating/deflating section 110 and the inner peripheral section 120.

As illustrated in FIGS. 1 and 2, the support section 130 possesses a cylindrical shape surrounding an internal space V2. The inner peripheral section 120, which forms a sealed state between the dilating/deflating section 110 and the inner peripheral section 120, is arranged in the internal space V2 of the support section 130.

The support section 130 is formed of sponge. For example, the sponge has a cellular structure of an open-cell type in which cells are formed on the surface of the sponge and the inside of the sponge, but is not limited to this. In addition, without being particularly limited, a material for forming the support section 130 includes various elastomers such as urethane, polyethylene, EPDM, and the like.

Next, a relationship between diameters of the dilating/deflating section 110 and the support section 130 will be described in detail. As illustrated in FIGS. 2(A) and 2(B), an inner diameter under atmospheric pressure (released state) of the dilating/deflating section 110 is D1, an outer diameter under atmospheric pressure of the support section 130 is D2, and an outer diameter of the support section 130 when the support section 130 is arranged inside the dilating/deflating section 110 under atmospheric pressure, in other words an inner diameter of the dilating/deflating section 110, is D3. In order to facilitate an understanding, FIGS. 2(A) and 2(B) omit the illustration of the thickness of the dilating/deflating section 110. In this case, the support section 130 is arranged inside the dilating/deflating section 110, thereby compressing the support section 130 and dilating (expanding) the dilating/deflating section 110. Therefore, a relationship of D1<D3<D2 is established. In addition, in view of the elasticity of the dilating/deflating section 110 and the compressive elasticity modulus of the support section 130, it is preferable to set the diameters D1 and D2 so that the diameter D3 substantially coincides with the inner diameter of an inner wall inside a lumen into which the balloon 100 is to be positioned. As an example of the diameter D1, the diameter D2, and the diameter D3, the diameter D3 is 12 mm, for example when the diameter D1 is 9 mm, and for example when the diameter D2 is 13 mm.

Referring back to FIG. 1, the fluid supply/discharge section 140 includes a tube 141 and a connector 142.

The tube 141 is flexible, and the distal end of the tube 141 is inserted into and fixed to a portion between the proximal side end portion 111 of the dilating/deflating section 110 and the inner peripheral section 120. The tube 141 communicates with the internal space V1 of the dilating/deflating section 110. As an example of a material for configuring the tube 141, it is possible to use the same material as that of the dilating/deflating section 110.

The connector 142 is attached to the proximal end of the tube 141. For example, the connector 142 is connected to a pressure control device such as a syringe and the like. An operation fluid is supplied from the pressure control device through the tube 141, thereby increasing pressure in the internal space V1 of the dilating/deflating section 110. On the other hand, the operation fluid is discharged to the pressure control device through the tube 141, thereby decreasing pressure in the internal space V1 of the dilating/deflating section 110. By way of example, the operation fluid is gas such as air and the like, for example. Alternatively, the operation fluid is a liquid such as distilled water, a physiological saline solution, and the like, for example. Furthermore, the pressure control device is configured to bring the internal space V1 of the dilating/deflating section 110 into a negative pressure state.

As described above, pressure in the internal space V1 of the dilating/deflating section 110 is caused to increase, thereby dilating the dilating/deflating section 110 outward in the radial direction, and deflating the inner peripheral section 120 inward in the radial direction. In addition, the internal space V1 of the dilating/deflating section 110 is brought into a negative pressure state, thereby deflating the dilating/deflating section 110 inward in the radial direction, and dilating the inner peripheral section 120 outward in the radial direction.

Next, an example will be described in which treatment for urethral stricture is performed on a stenosed site in a lumen using the balloon 100.

Figure 4:
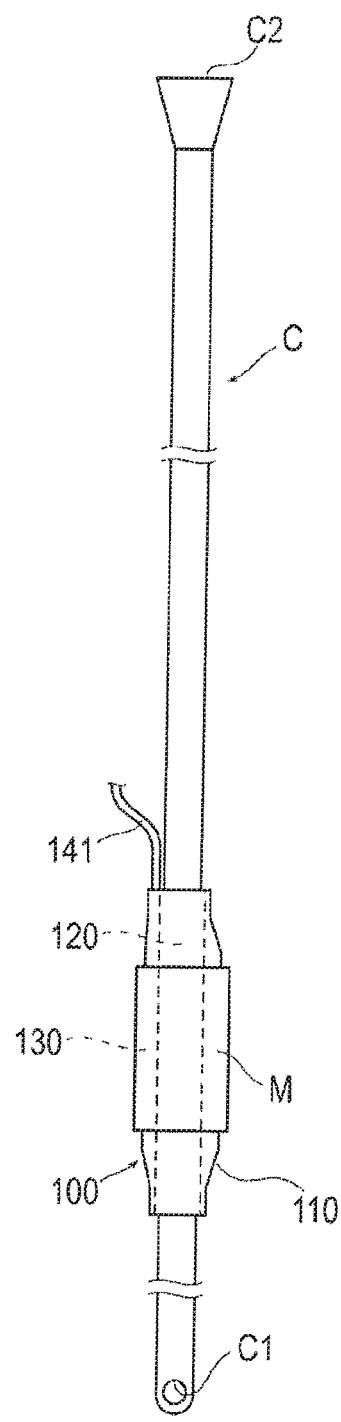
FIG. 4 is a view illustrating a state where the balloon is attached to a urethral catheter.
Figure 5:
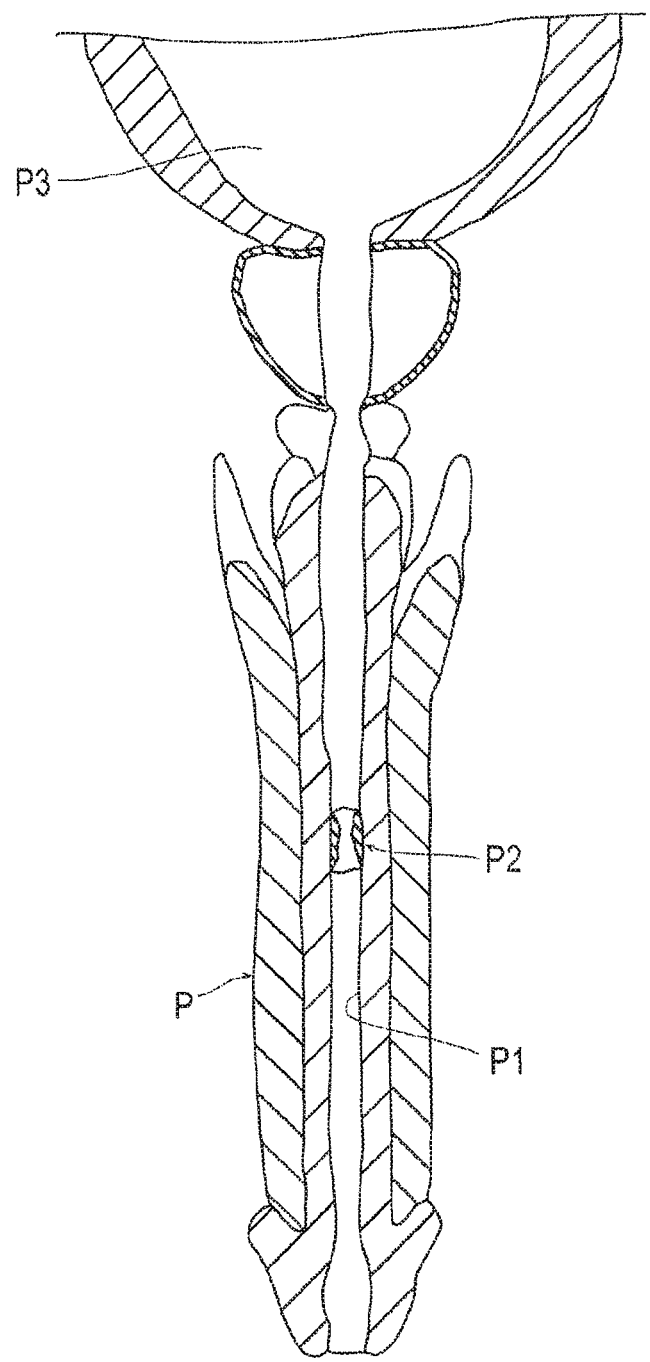
FIG. 5 is a cross-sectional view illustrating a urethra having a stenosed site, together with a bladder.
Figure 6:
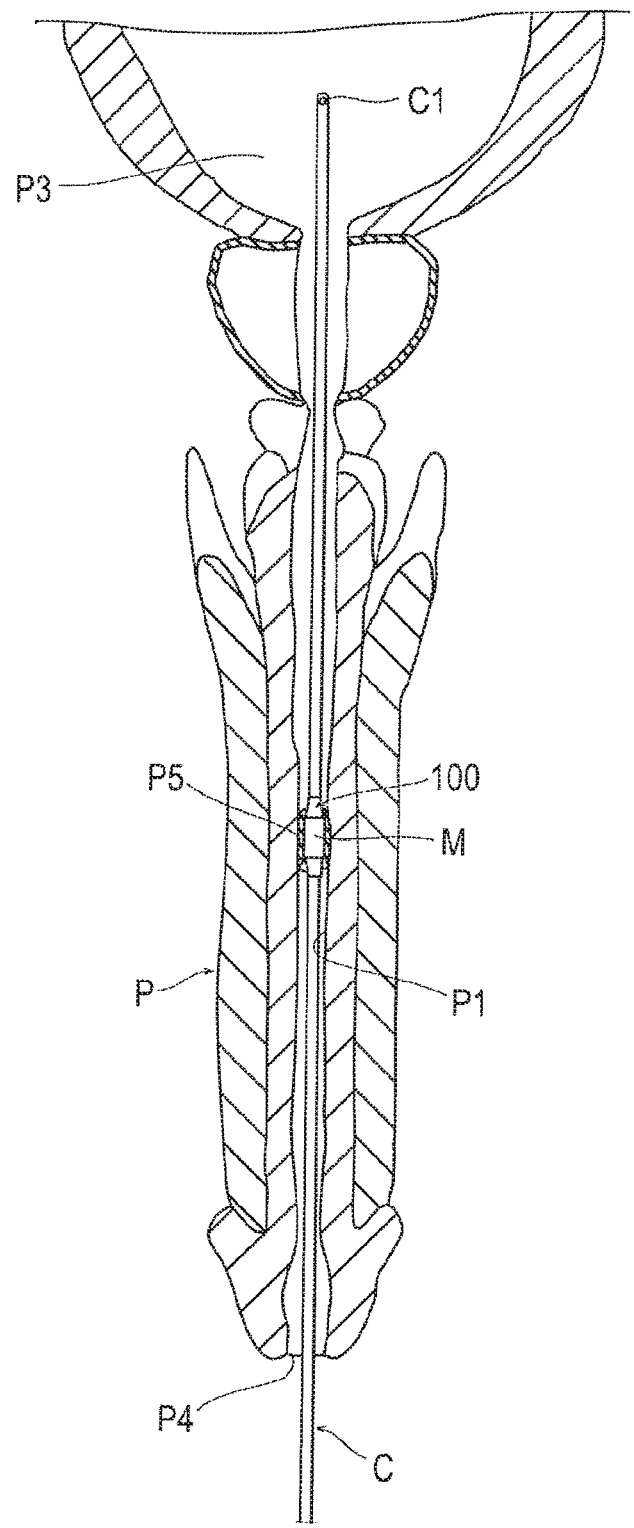
FIG. 6 is a view illustrating a state where the balloon together with the urethral catheter is inserted into the urethra.

FIG. 4 is a view illustrating a state where the balloon 100 according to the present embodiment is attached to or mounted on a urethral catheter C. FIG. 5 is a sectional view illustrating a urethra P1 having a stenosed site P2, together with a bladder P3. FIG. 6 is a view illustrating a state where the balloon 100 together with the urethral catheter C is inserted into the urethra P1.

As illustrated in FIG. 4, the balloon 100 is used together with the urethral catheter C.

The urethral catheter C has a tubular shape, and is flexible. An opening portion C1 is formed on an outer periphery near the distal end of the urethral catheter C. In addition, an opening portion C2 is also formed on the proximal end of the urethral catheter C. The opening portion C1 communicates with the inside of the urethral catheter C (i.e., a lumen extending throughout the length of the urethral catheter C) and also communicates with the opening portion C2 of the urethral catheter C. As the urethral catheter C, it is possible to use a known one in the related art.

The urethral catheter C is attached to the balloon 100 through an inner periphery of the inner peripheral section 120. That is, the urethral catheter C passes through the lumen in the inner peripheral section. When the urethral catheter C is inserted into the inner periphery of the inner peripheral section 120, the internal space V1 of the dilating/deflating section 110 is in a negative pressure state through operation of the pressure control device connected to the connector 142. In this manner, the inner peripheral section 120 is dilated in the radial outward direction before inserting the balloon 100 into the lumen in the living body, thereby improving insertion performance (i.e., facilitating insertion of the urethral catheter C).

A medical material M which provides an epithelial function is arranged on the outer periphery of the balloon 100. The medical material M has a shape in which a sheet is formed into a cylindrical shape. The medical material M is obtained by processing epithelial tissues collected from a living body. The epithelial tissues may be collected from any site of the living body, but it is preferable to use an oral mucosa. The oral mucosa includes epithelial cells.

As illustrated in FIG. 5, the urethral stricture is a disease in which the stenosed site P2 is formed in the urethra P1 inside a penis P by scar tissue. The scar tissue is formed since a mucosa of the urethra P1 or a corpus spongiosum surrounding the mucosa of the urethra P1 is scarred while an injury to the mucosa of the urethra P1 is recovering.

First, an operator inserts an endoscope into the urethra P1, and performs treatment such as dissection, cutting, excision, and the like on the stenosed site P2 via the endoscope. After the treatment, the operator removes the endoscope.

Thereafter, the operator inserts the balloon 100 together with the urethral catheter C (i.e., the arrangement shown in FIG. 4)) into the urethra P1 through an external urethral orifice P4 as illustrated in FIG. 6, and arranges the balloon 100 in a treatment side P5 (inserting process). During this inserting process, the medical material M is positioned on the outer periphery of the balloon 100. At this time, the internal space V1 of the dilating/deflating section 110 is brought into a negative pressure state through operation of the pressure control device connected to the connector 142, thereby bringing the balloon 100 into a deflated state. The treatment site P5 is a site from which the scar tissue is removed by performing the above-described treatment such as dissection and the like on the stenosed site P2. The opening portion C1 at the distal end of the urethral catheter C is arranged inside the bladder P3. Urine accumulated in the bladder P3 is discharged to the proximal end of the urethral catheter C through the opening portion C1.

After the opening portion C1 is arranged inside the bladder P3 and the balloon 100 is arranged in the treatment site P5, the operator releases the negative pressure state in the internal space V1 of the dilating/deflating section 110 through operation of the pressure control device connected to the connector 142. Since the negative pressure state in the internal space V1 of the dilating/deflating section 110 is released, pressure in the internal space V1 becomes higher than pressure in the internal space V1 during the inserting process. In this manner, as illustrated in FIG. 2, the support section 130 arranged inside the dilating/deflating section 110 dilates the dilating/deflating section 110 outward. In response to the dilation, the medical material M is compressed by being pressed against the treatment site P5 (dilating process). That is, since the support section 130 is arranged inside the dilating/deflating section 110, the dilating/deflating section 110 is dilated without pressurizing the internal space V1 of the dilating/deflating section 110. Accordingly, it is possible to maintain the dilated state. In accordance with a stenosed state of the stenosed site P2, a degree of the negative pressure state in the internal space V1 of the dilating/deflating section 110 may be adjusted. In this manner, the outer diameter of the dilating/deflating section 110 after releasing the negative pressure state may be adjusted, or if necessary, the internal space V1 of the dilating/deflating section 110 may be pressurized. In addition, although not illustrated in FIG. 6, the tube 141 which communicates with the inside of the balloon 100 is held in a state where the tube 141 is drawn out to the outside of the body from the external urethral orifice P4 through the inside of the urethra P1.

If the treatment site P5 is exposed to a liquid such as urine and the like, there is a possibility that a scar tissue may be hypertrophied and the urethral stricture may recur. Accordingly, it is not desirable to expose the treatment site P5. According to the present embodiment, the medical material M compresses the treatment site P5, thereby allowing an epithelial cell to be regenerated or engrafted in the treatment site P5. In this manner, the epithelial function is provided (granted and acquired). Specifically, the epithelial function includes a function to protect the treatment site P5 from a liquid (urine or inflammatory inducing components), other biological secretions, bacteria, or the like.

After the medical material M is brought into pressing contact with the treatment site P5, an operator deflates the balloon 100, and removes the balloon 100 together with the urethral catheter C from the urethra P1.

Through the above-described processes, the treatment is performed.

As described above, the balloon 100 according to this embodiment has the dilating/deflating section 110 that forms the hollow internal space V1, and that deflates (i.e., becomes small]r) by the internal space V1 being decompressed, and the support section 130 that is arranged in the internal space V1 so as to deflate in response to the deflation of the dilating/deflating section 110, and that supports the dilating/deflating section 110 so as to dilate outward in a state where the internal space V1 is under atmospheric pressure. Therefore, without pressurizing the balloon 100, a dilated state of the balloon 100 can be maintained. Accordingly, the balloon 100 can be rather easily pressed against the treatment site P5 inside the urethra P1. In addition, the support section 130 is disposed in order to dilate the dilating/deflating section 110 so as to have a predetermined outer diameter. In this manner, while wrinkles on the outer surface of the dilating/deflating section 110 are reduced, the balloon 100 can be pressed against the treatment site P5 inside the urethra P1 by using proper pressing force. Therefore, it is possible to provide the balloon 100 which can be easily pressed against the treatment site P5 inside the urethra P1 by using proper pressing force.

In addition, the support section 130 has the outer diameter having a columnar shape which forms a circular cross section. The outer diameter D2 of the support section 130 is configured to be larger than the inner diameter D1 of the dilating/deflating section 110 under atmospheric pressure. Therefore, the dilating/deflating section 110 can uniformly dilate outward in the radial direction, along the circumferential direction of the dilating/deflating section 110. Accordingly, when the medical material M is brought into pressing contact with the treatment site P5, it is possible to suitably prevent wrinkles from being formed on the dilating/deflating section 110, and it is possible to more suitably bring the medical material M into pressing contact with the treatment site P5.

In addition, the support section 130 possesses a cylindrical shape having the internal space V2 therein. The inner peripheral section 120 which forms a sealed state between the dilating/deflating section 110 and the inner peripheral section 120 is arranged in the internal space V2 of the support section 130. The inner peripheral section 120 dilates or deflates in the radial direction in response to an increase or a decrease in the pressure in the internal space V1 between the dilating/deflating section 110 and the inner peripheral section 120. Therefore, in accordance with the dilation and deflation of the inner peripheral section 120, a holding force for holding the urethral catheter C inserted into the inner peripheral section 120 is configured to be variable. For example, the inner peripheral section 120 is dilated and the holding force is weakened, thereby facilitating relative alignment between the urethral catheter C and the balloon 100, and attachment or detachment therebetween. In addition, when the urethral catheter C and the balloon 100 are caused to indwell at a desired position in the urethra P1, the inner peripheral section 120 is deflated and the holding force is strengthened. In this manner, it is possible to suitably prevent misalignment of the urethral catheter C (relative movement of the urethral catheter C and the balloon 100).

In addition, the inner peripheral section 120 deflates in the radial direction by increasing the pressure in the internal space V1 between the dilating/deflating section 110 and the inner peripheral section 120. Therefore, it is possible to suitably prevent misalignment of the urethral catheter C by strengthening the holding force for holding the urethral catheter C positioned in the inner periphery of the inner peripheral section 120.

In addition, the inner peripheral section 120 dilates in the radial outward direction by decreasing the pressure in the internal space V1 between the dilating/deflating section 110 and the inner peripheral section 120. Therefore, the urethral catheter C having the relatively large outer diameter can be inserted into the inner peripheral section 120.

In addition, as described above, the intraluminal treatment method according to the present embodiment includes the insertion step of inserting the balloon 100 into the urethra P1 by bringing the internal space V1 into a negative pressure state, the balloon 100 including the dilating/deflating section 110 that forms the hollow internal space V1, and that deflates by the internal space V1 being decompressed, and the support section 130 that is arranged in the internal space V1 so as to deflate in response to the deflation of the dilating/deflating section 110, and that supports the dilating/deflating section 110 so as to dilate outward in a state where the internal space V1 is under atmospheric pressure, and the dilation step of causing the support section 130 to dilate the dilating/deflating section 110 in the radial direction by releasing a negative pressure in the internal space V1. Therefore, without pressurizing the balloon 100, a dilated state of the balloon 100 can be maintained. Accordingly, the balloon 100 can be relatively easily pressed against the treatment site P5 inside the urethra P1. In addition, the support section 130 is disposed in order to dilate the dilating/deflating section 110 so as to have a desired outer diameter. In this manner, while wrinkles on the outer surface of the dilating/deflating section 110 are reduced, the balloon 100 can be pressed against the treatment site P5 inside the urethra P1 by using proper pressing force. Therefore, it is possible to provide the intraluminal treatment method in which balloon 100 can be rather easily pressed against the treatment site P5 inside the urethra P1 by using proper pressing force.

In addition, the balloon 100 further has the inner peripheral section 120 which is arranged in the internal space V2 of the support section 130 so as to form a sealed state between the dilating/deflating section 110 and the inner peripheral section 120. In the inserting process, the inner peripheral section 120 dilates in the radial outward direction by bringing the internal space V1 of dilating/deflating section 110 into a negative pressure state. In the dilating process, the inner peripheral section 120 deflates in the radial direction by releasing a negative pressure in the internal space V1 of dilating/deflating section 110. Therefore, the urethral catheter C having the relatively large outer diameter can be inserted into the inner peripheral section 120. It is possible to suitably prevent misalignment of the urethral catheter C by strengthening the holding force holding the urethral catheter C inserted into the inner periphery of the inner peripheral section 120.

Hereinafter, a modification example relating to a support section according to the above-described embodiment will be described as another example of the balloon disclosed here.

Figure 7:
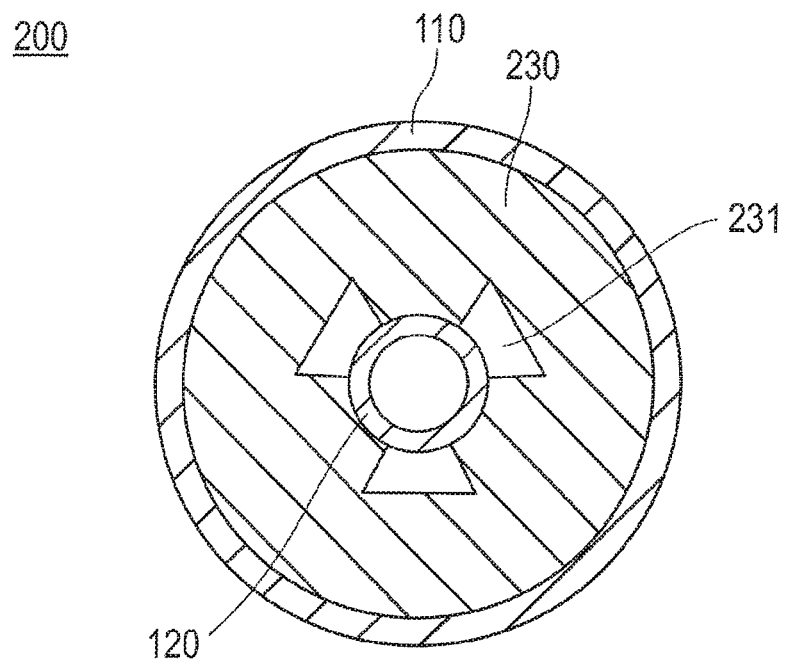
FIG. 7 is a view of a balloon according to Modification Example 1, which corresponds to FIG. 3.

FIG. 7 is a view of a balloon 200 according to Modification Example 1, which corresponds to FIG. 3. The balloon 200 according to Modification Example 1 has the dilating/deflating section 110, the inner peripheral section 120, and a support section 230. The dilating/deflating section 110 and the inner peripheral section 120 have the same configuration as those according to the above-described embodiment. As illustrated in FIG. 7, the support section 230 according to Modification Example 1 has a weak portion 231 (relatively weaker portion) whose rigidity is lower than that of the other portions. For example, the weak portion 231 is a wedge-shaped gap disposed on an inner peripheral side of the support section 230. According to this configuration, the weak portion 231 is provided. Therefore, when the internal space V1 of the dilating/deflating section 110 is brought into a negative pressure state so as to deflate the dilating/deflating section 110, the dilating/deflating section 110 can be more uniformly deflated in the circumferential direction.

Figure 8:
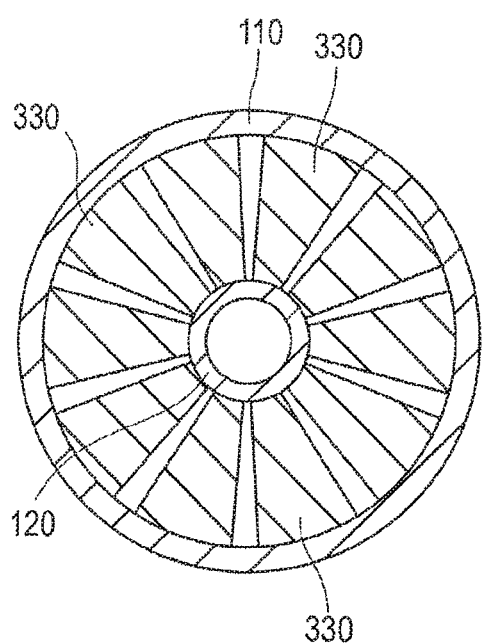
FIG. 8 is a view of a balloon according to Modification Example 2, which corresponds to FIG. 3.

FIG. 8 is a view of a balloon 300 according to Modification Example 2, which corresponds to FIG. 3. The balloon 300 according to Modification Example 2 has the dilating/deflating section 110, the inner peripheral section 120, and a support section 330. The dilating/deflating section 110 and the inner peripheral section 120 have the same configuration as those according to the above-described embodiment. According to the above-described embodiment, the support section 130 has the cylindrical shape which forms the circular cross section. However, without being limited thereto, as illustrated in FIG. 8, a configuration may be adopted in which the support section 330 is divided into multiple portions in the circumferential direction. According to this configuration, the support section 330 has a configuration in which the support section 330 is divided into the multiple portions. Therefore, when the internal space V1 of the dilating/deflating section 110 is brought into a negative pressure state so as to deflate the dilating/deflating section 110, the dilating/deflating section 110 can be more uniformly deflated in the circumferential direction.

Figure 9A:
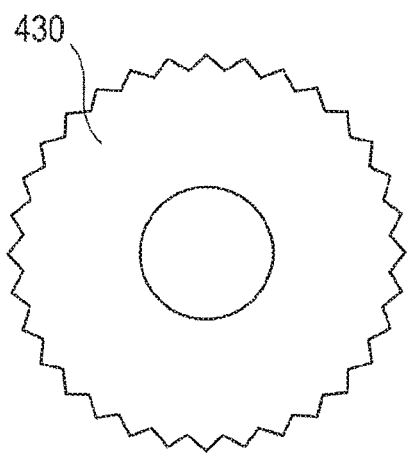
FIGS. 9(A) and 9(B) are cross-sectional and perspective views respectively illustrating a support section according to Modification Example 3.
Figure 9B:
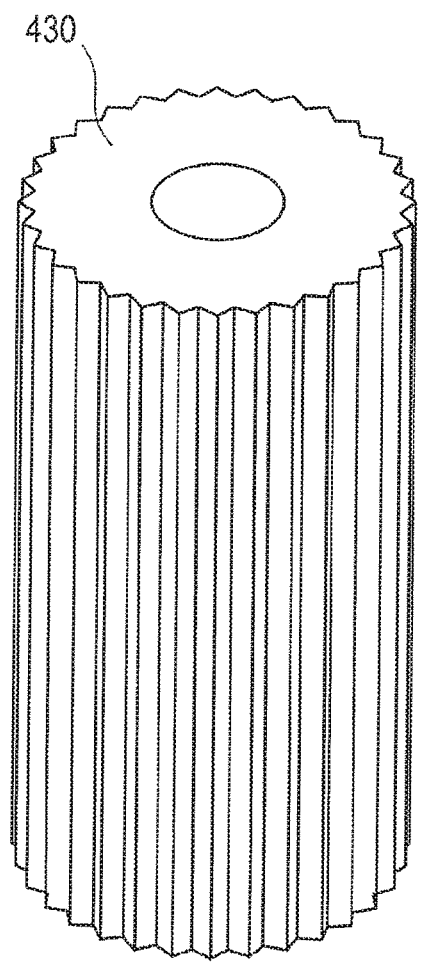

FIGS. 9(A) and 9(B) are views illustrating a support section 430 according to Modification Example 3. FIG. 9(A) is a top view, and FIG. 9(B) is a perspective view, respectively. According to the above-described embodiment, the support section 130 has the cylindrical shape which forms the circular cross section. However, without being limited thereto, as illustrated in FIGS. 9(A) and 9(B), the support section 430 may employ a shape in which the outer periphery of the cross section has an uneven shape (undulating shape in transverse cross-section). In this illustrated modification example, the transverse cross-section includes a plurality of alternating pointed (sharp) peaks and valleys arranged in an annular manner and forming a saw-tooth pattern. According to this configuration, flex resistance is improved, and the medical material M can be brought into pressing contact with the treatment site P5 inside the urethra P1 by using flexible pressing pressure. Furthermore, according to this configuration, the outer periphery has the uneven shape. Therefore, when the medical material M is pressed against the treatment site P5, both of these come into linear or point contact with each other without coming into surface contact therebetween. Accordingly, it is possible to avoid a problem of ischemia caused by excessive compression.

Figure 10A:
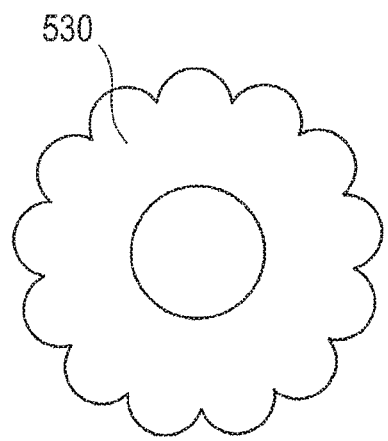
FIGS. 10(A) and 10(B) are cross-sectional and perspective views respectively illustrating a support section according to Modification Example 4.
Figure 10B:
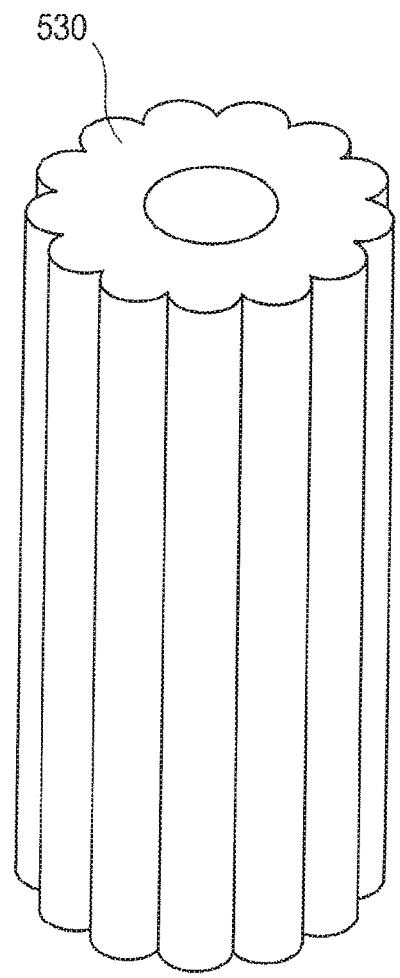

FIGS. 10(A) and 10(B) are views illustrating a support section 530 according to Modification Example 4. FIG. 10(A) is a top view, and FIG. 10(B) is a perspective view, respectively. According to the above-described embodiment, the support section 130 has the cylindrical shape which forms the circular cross section. However, without being limited thereto, as illustrated in FIGS. 10(A) and 10(B) the support section 530 may employ a shape in which the outer periphery of the cross section has an uneven shape (undulating shape in transverse cross-section). In this illustrated modification example, the transverse cross-section includes a plurality of alternating rounded peaks and valleys arranged in an annular manner. According to this configuration, flex resistance is improved, and the medical material M can be brought into pressing contact with the treatment site P5 inside the urethra P1 by using flexible pressing pressure. Furthermore, according to this configuration, the outer periphery has the uneven shape. Therefore, when the medical material M is pressed against the treatment site P5, both of these come into linear or point contact with each other without coming into surface contact therebetween. Accordingly, it is possible to avoid a problem of ischemia caused by excessive compression.

Figure 11A:
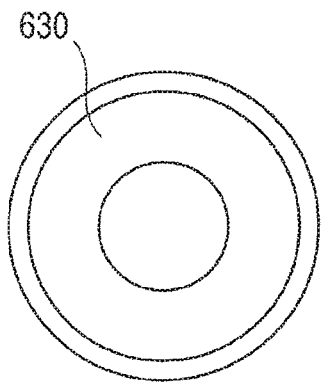
FIGS. 11(A) and 11(B) are cross-sectional and perspective views respectively illustrating a support section according to Modification Example 5.
Figure 11B:
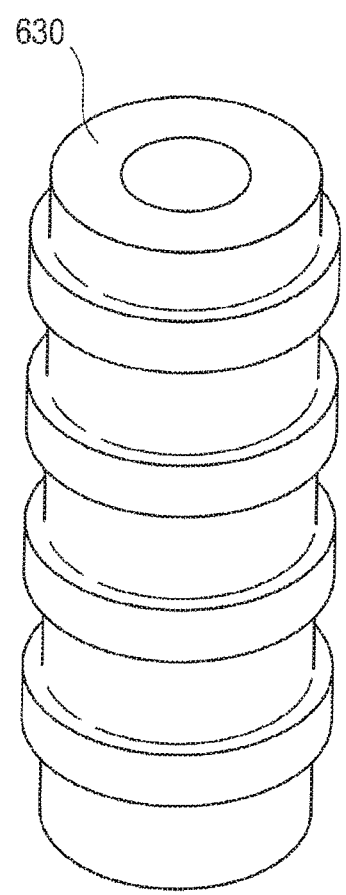

FIGS. 11(A) and 11(B) are views illustrating a support section 630 according to Modification Example 5. FIG. 11(A) is a top view, and FIG. 11(B) is a perspective view, respectively. According to the above-described embodiment, the support section 130 has the cylindrical shape which is uniform in the axial direction. However, without being limited thereto, as illustrated in FIGS. 11(A) and 11(B), the support section 630 may employ a shape having different circular cross sections in the axial direction. In this illustrated modification example, the support section includes a plurality of axially arranged annular portions of alternating larger and smaller outer diameters. According to this configuration, flex resistance is improved, and the medical material M can be brought into pressing contact with the treatment site P5 inside the urethra P1 by using flexible pressing pressure. Furthermore, according to this configuration, the outer periphery has the uneven shape. Therefore, when the medical material M is pressed against the treatment site P5, both of these come into linear or point contact with each other without coming into surface contact therebetween. Accordingly, it is possible to avoid a problem of ischemia caused by excessive compression.

Figure 12:
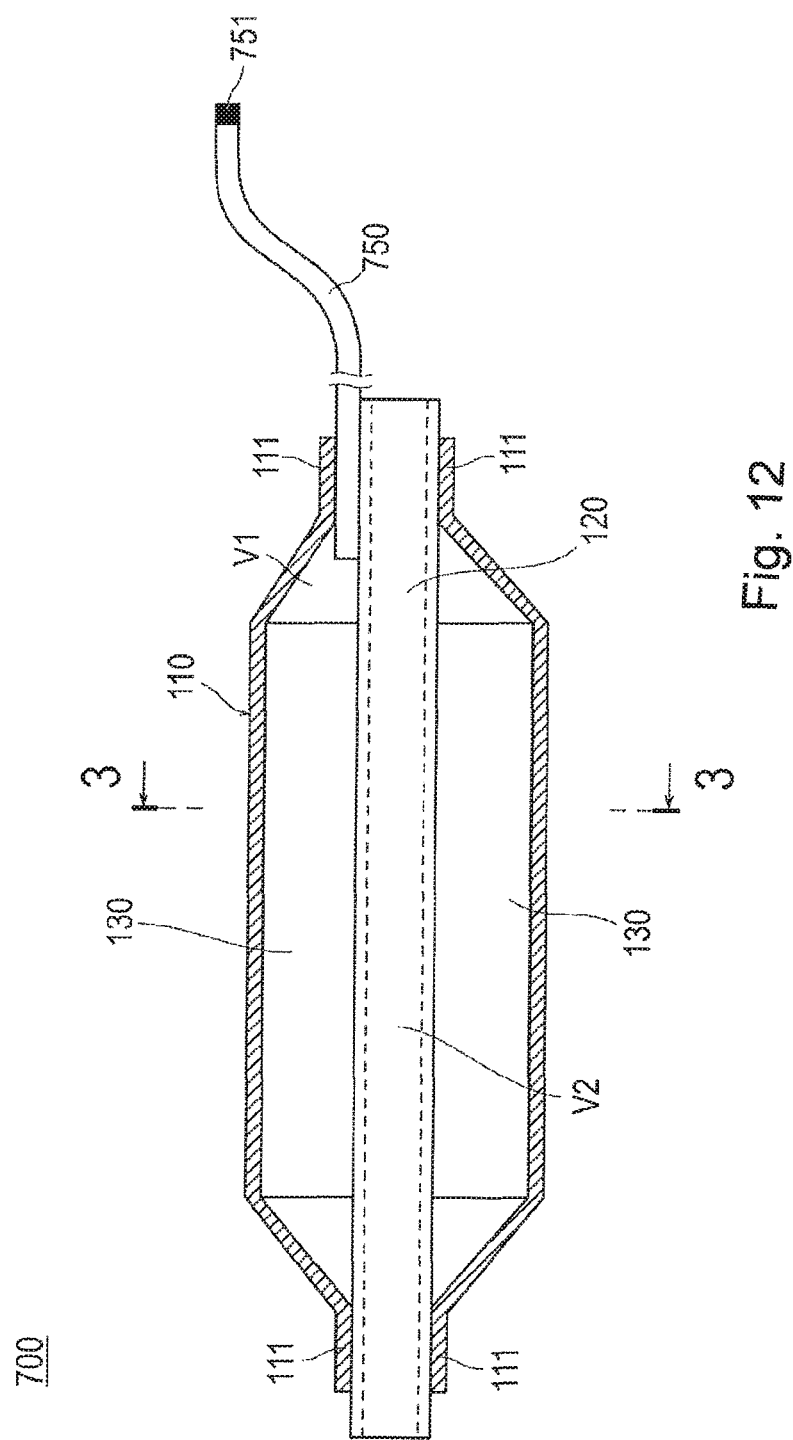
FIG. 12 is a view illustrating a support section according to Modification Example 6.

FIG. 12 is a view illustrating a balloon 700 according to Modification Example 6. In the balloon 700 according to Modification Example 6, the internal space V1 of the dilating/deflating section 110 maintains a negative pressure state. When the balloon 700 is supplied as a product, in order to miniaturize the product and to prevent physical properties from being degenerated (degraded) due to pressure continuously applied to the material, it is preferable that the balloon 700 maintains the negative pressure state. As illustrated in FIG. 12, the balloon 700 according to Modification Example 6 has a fluid supply/discharge section 750 which communicates with the internal space V1 of the dilating/deflating section 110. A negative pressure releasing portion 751 which releases a negative pressure state maintained in the internal space V1 of the dilating/deflating section 110 is disposed in the proximal end portion of the fluid supply/discharge section 750. For example, the negative pressure releasing portion 751 is a connector on which a sealing process is performed in order to maintain a sealed state. A negative pressure state in the internal space V1 of the dilating/ deflating section 110 is released by unsealing the connector. As a result, the dilating/deflating section 110 dilates outward, and the medical material M is brought into pressing contact with the treatment site P5. When the balloon 700 is removed from the urethra P1, the connector whose sealed state is released deflates the dilating/deflating section 110 in such a way that a pressure control device such as a syringe and the like brings the internal space V1 of the dilating/deflating section 110 into a negative pressure state again. The negative pressure releasing portion 751 is not limited to the connector on which the sealing process is performed. For example, a valve body arranged on the proximal side of the fluid supply/discharge section 750 or a structural body such as a three-way stopcock and the like may be used. Alternatively, a configuration may be adopted which uses a weak structure which facilitates cutting, twisting, drilling, folding, or the like. As described above, by maintaining a negative pressure state in the internal space V1 of the dilating/deflating section 110, it is possible to suitably prevent force acting outward in the radial direction from being applied to the dilating/deflating section 110. Therefore, it is possible to suitably prevent the dilating/deflating section 110 from being plastically deformed.

The present invention is not limited to the above-described embodiment or modification examples, and can be modified in various ways within the scope of claims.

Figure 13:
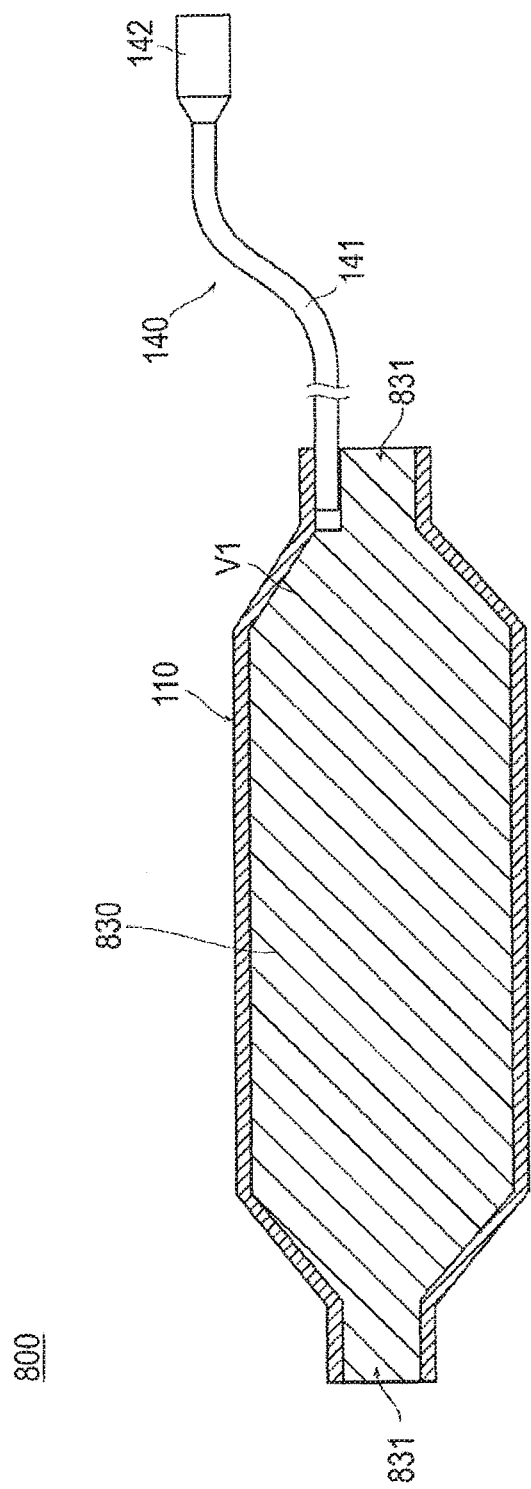
FIG. 13 is a view illustrating a balloon in which a support section is solid.

For example, according to the above-described embodiment, the balloon 100 has the inner peripheral section 120 inside the support section 130. However, without being limited thereto, a configuration of the balloon 100 is not particularly limited as long as a configuration is adopted in which the support section 130 is arranged inside the dilating/deflating section 110 and the support section 130 dilates the dilating/deflating section 110 outward in the radial direction under atmospheric pressure. For example, as illustrated in FIG. 13, a balloon 800 may not have the inner peripheral section 120, and a support section 830 may be solid. In this case, for example, it is preferable to seal both end portions 831 in the axial direction of the support section 830 so as to be liquid-tight and air-tight by using a sealing method of adhesive coating or a heat sealing method.

In addition, according to the above-described embodiment, the balloon 100 is used for urethral stricture treatment. However, without being limited thereto, the balloon 100 can be applied to PTA balloon catheter, tracheostomy tube, gastrostomy, urinary catheter, bladder fistula catheter, nephrostomy catheter, sinusitis treatment balloon, gastric varix hemostasis balloon catheter, uterine hemostasis catheter, various drainage tubes, and the like.

The detailed description above describes a balloon and an intraluminal treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon comprising:
   a dilating/deflating section that forms a hollow internal space, and that is configured to deflate by the hollow internal space being decompressed; and
   a support section configured to be arranged in the hollow internal space;
   pressure means for increasing or decreasing pressure in the hollow internal space of the dilating/deflating section;
   wherein, when the support section is arranged in the hollow internal space, the support section is configured to deflate in response to the deflation of the dilating/deflating section, and to support the dilating/deflating section so as to dilate outward in a state where the hollow internal space is under atmospheric pressure;
   wherein the support section possesses a columnar outer shape which forms a circular cross-section,
   wherein, when the support section is under atmospheric pressure and not arranged in the hollow internal space, an outer diameter of the support section is larger than an inner diameter of the dilating/deflating section, and
   further comprising an inner peripheral section positioned in the hollow internal space, the inner peripheral section being sealed to the dilating/deflating section, and
   wherein the inner peripheral section dilates outwardly in a radial direction in response to a decrease in pressure in the hollow internal space and wherein the inner peripheral section deflates inwardly in the radial direction in response to an increase in pressure in the hollow internal space.

2. The balloon according to claim 1, wherein the support section has a relatively weaker portion whose rigidity is lower than that of other portions of the support section.

3. The balloon according to claim 1, further comprising:
   a fluid supply/discharge section that communicates with the internal space of the dilating/deflating section, and
   a negative pressure releasing portion, which releases a negative pressure state in the internal space of the dilating/deflating section, disposed on a proximal side of the fluid supply/discharge section.

4. The balloon according to claim 1, wherein the support section includes a plurality of circumferentially arranged wedge-shaped gaps on an inner peripheral side of the support section.

5. The balloon according to claim 1, wherein the support section possesses an outer surface that is an undulating surface as seen in transverse cross-section.

6. A balloon comprising:
   a dilating/deflating section that forms a hollow internal space, and that is configured to deflate by the hollow internal space being decompressed; and
   a support section configured to be arranged in the hollow internal space;
   wherein the support section is arranged in the hollow internal space such that the support section is configured to deflate in response to the deflation of the dilating/deflating section, and to support the dilating/deflating section so as to dilate outward in a state where the hollow internal space is under atmospheric pressure;
   wherein the support section possesses a cylindrical shape surrounding an internal space,
   further comprising an inner peripheral section positioned in the internal space of the support section, the inner peripheral section being sealed to the dilating/deflating section, and
   wherein the inner peripheral section dilates outwardly in a radial direction in response to a decrease in pressure in an internal space between the dilating/deflating section and the inner peripheral section and wherein the inner peripheral section deflates inwardly in the radial direction in response to an increase in pressure in the internal space between the dilating/deflating section and the inner peripheral section.

7. An intraluminal treatment method comprising:
creating a negative pressure in a hollow internal space surrounded by a dilating/deflating section of a balloon, and including a support section positioned in the hollow internal space;
inserting the balloon into a lumen in a living body while the hollow internal space is under the negative pressure; and
releasing the negative pressure in the hollow internal space to cause the support section to dilate outwardly in a radial direction and press against the dilating/deflating section so that the dilating/deflating section is expanded outwardly into contact with an inner surface of the lumen in the living body;
an inner peripheral section being positioned in an internal space of the support section and the inner peripheral section being sealed to the dilating/deflating section, and
wherein the inner peripheral section dilates outwardly in a radial direction in response to a decrease in pressure in an internal space between the dilating/deflating section and the inner peripheral section and wherein the inner peripheral section deflates inwardly in the radial direction in response to an increase in pressure in the internal space between the dilating/deflating section and the inner peripheral section.

8. The intraluminal treatment method according to claim 7,
wherein a sealed state exists between the dilating/deflating section and the inner peripheral section,
wherein the creation of the negative pressure in the hollow internal space causes the inner peripheral section to dilate outwardly in the radial direction, and
wherein the releasing of the negative pressure in the hollow internal space causes the inner peripheral section to deflate inwardly in the radial direction.

9. The intraluminal treatment method according to claim 7, wherein the releasing of the negative pressure in the hollow internal space to cause the support section to dilate outwardly in the radial direction and press against the dilating/deflating section comprises increasing the pressure in the hollow internal space to atmospheric pressure.

10. The intraluminal treatment method according to claim 7, wherein the inserting of the balloon into the lumen in the living body includes inserting the balloon into the urethra.

11. The intraluminal treatment method according to claim 7, wherein a sealed state exists between the dilating/deflating section and the inner peripheral section,
the creation of the negative pressure in the hollow internal space causing the inner peripheral section to dilate radially outwardly,
the method further comprising, after creating the negative pressure in the hollow internal space and before inserting the balloon into the lumen in the living body, inserting a catheter into the inner peripheral section, the catheter being movable relative to the inner peripheral section.

12. The intraluminal treatment method according to claim 11, wherein the releasing of the negative pressure in the hollow internal space comprises releasing the negative pressure in the hollow internal space while the catheter is positioned in the inner peripheral section, and wherein the releasing of the negative pressure in the hollow internal space causes the inner peripheral section to deflate inwardly in the radial direction so that the catheter is held by the inner peripheral section.

13. An intraluminal treatment method comprising:
inserting a balloon into a lumen in a living body while a hollow internal space surrounded by a dilating/deflating section of the balloon is under the negative pressure, the dilating/deflating section of the balloon possessing an outer surface;
increasing the pressure in the hollow internal space to a pressure greater than the negative pressure in the hollow internal space during insertion of the balloon into the lumen in the living body; and
the increase of the pressure in the hollow internal space causing a support section located in the hollow internal space to press outwardly against the dilating/deflating section so that the outer surface of the dilating/deflating section contacts an inner surface of the lumen in the living body;
an inner peripheral section being positioned in an internal space of the support section and the inner peripheral section being sealed to the dilating/deflating section, and
wherein the inner peripheral section dilates outwardly in a radial direction in response to a decrease in pressure in an internal space between the dilating/deflating section and the inner peripheral section and wherein the inner peripheral section deflates inwardly in the radial direction in response to an increase in pressure in the internal space between the dilating/deflating section and the inner peripheral section.

14. The intraluminal treatment method according to claim 13, wherein the increasing of the pressure in the hollow internal space comprises increasing the pressure in the hollow internal space to atmospheric pressure.

15. The intraluminal treatment method according to claim 13, wherein a sealed state exists between the dilating/deflating section and the inner peripheral section, and
the inner peripheral section being dilated radially outwardly while the hollow internal space is under the negative pressure,
the method further comprising, while the hollow internal space is under the negative pressure and before inserting the balloon into the lumen in the living body, inserting a catheter into the inner peripheral section, the catheter being movable relative to the inner peripheral section.

16. The intraluminal treatment method according to claim 15, wherein the increase of the pressure in the hollow internal space causes the inner peripheral section to deflate inwardly in the radial direction so that the catheter is held by the inner peripheral section.

* * * * *